United States Patent [19]

Querals et al.

[11] Patent Number: 5,290,295

[45] Date of Patent: Mar. 1, 1994

[54] INSERTION TOOL FOR AN INTRALUMINAL GRAFT PROCEDURE

[75] Inventors: Luis A. Querals, Baltimore, Md.; Michael J. Fine, Coral Springs, Fla.

[73] Assignee: Querals & Fine, Inc., Coral Springs, Fla.

[21] Appl. No.: 913,208

[22] Filed: Jul. 15, 1992

[51] Int. Cl.⁵ .............................................. A61M 29/00
[52] U.S. Cl. ...................................... 606/108; 623/1; 623/12; 606/31; 606/194; 604/264
[58] Field of Search .............................. 606/1, 27–31, 606/108, 192, 194; 604/164, 165, 171, 263, 264; 623/1, 12

[56] References Cited

U.S. PATENT DOCUMENTS

| | | | |
|---|---|---|---|
| 4,512,338 | 4/1985 | Balko et al. | 606/108 |
| 4,654,024 | 3/1987 | Crittenden et al. | 606/31 |
| 4,665,918 | 5/1987 | Garza et al. | |
| 4,732,152 | 5/1988 | Wallsten et al. | |
| 4,739,762 | 4/1988 | Palmaz | 673/1 |
| 4,771,773 | 9/1988 | Kropf | |
| 4,787,899 | 11/1988 | Lazarus | |
| 4,875,480 | 10/1989 | Imbert | |
| 5,037,427 | 8/1991 | Harada et al. | 623/1 |
| 5,092,877 | 3/1992 | Pinchuk | 623/1 |
| 5,108,407 | 4/1992 | Geremia et al. | 623/12 |
| 5,147,370 | 9/1992 | McNamara et al. | 606/108 |

*Primary Examiner*—Stephen C. Pellegrino
*Assistant Examiner*—Glenn Dawson
*Attorney, Agent, or Firm*—Harry W. Barron

[57] ABSTRACT

A tool for the intraluminal insertion and deployment of a tubular graft within a blood vessel includes a flexible insertion shaft with a tapered distal end, a tubular sheath, a deployment slider and a safety locking tube. The deployment slider and the graft are slideably mounted, end to end, on a cylindrical portion of the shaft. A tubular sheath, which is slideably mounted to cover the graft and a distal portion of the deployment slider, includes a tapered distal end portion with tabs extending into a circumferential groove in the shaft. The graft is deployed, or released, by first removing the safety lock tube and then the tubular sheath is withdrawn over the proximal end of the shaft, exposing the graft from the outside and from the distal end of the tool. Then the shaft is then withdrawn as the deployment slider is held in place to prevent the withdrawal of the graft. Prior to deployment, the safety locking tube is locked on the proximal end of the shaft in an end to end relationship with the tubular sheath, thereby preventing premature deployment by preventing the withdrawal of the tubular sheath. An alternative version of the tool includes an electrical heating element to aid in the softening and dilating of tissues, and a second alternative version of the tool includes an angioplasty balloon at the distal end, so that obstructions can be cleared by angioplasty as the tool is advanced along a blood vessel.

20 Claims, 4 Drawing Sheets

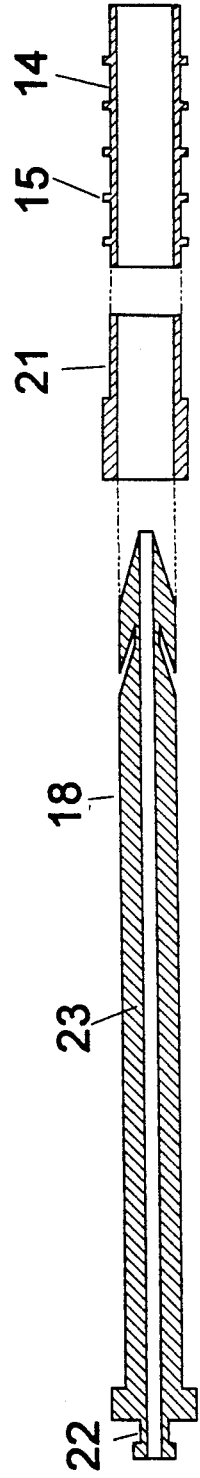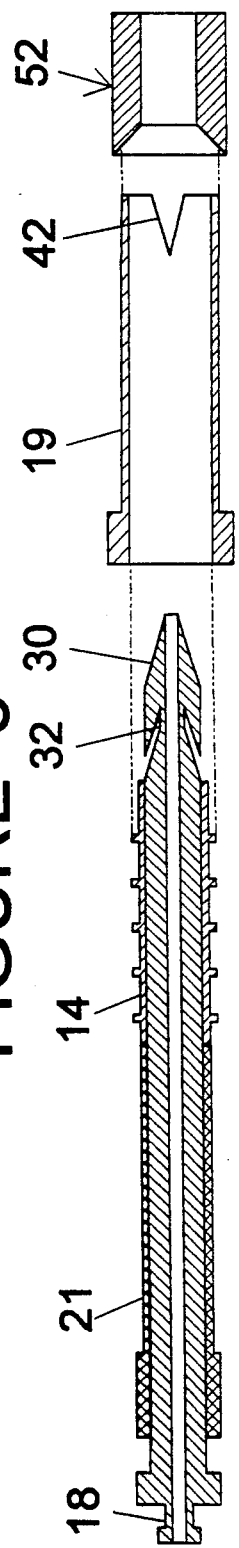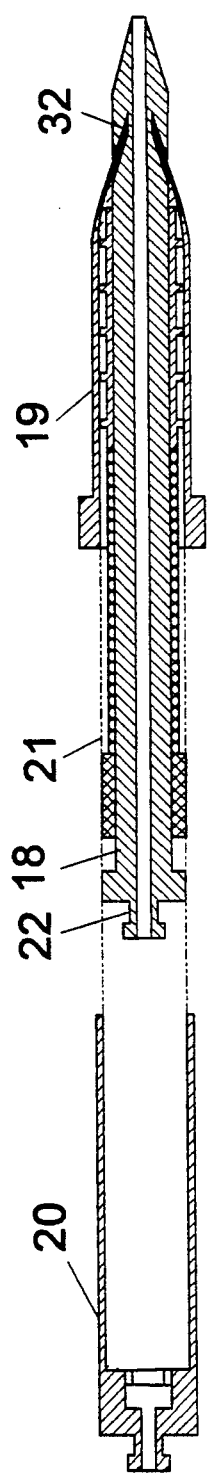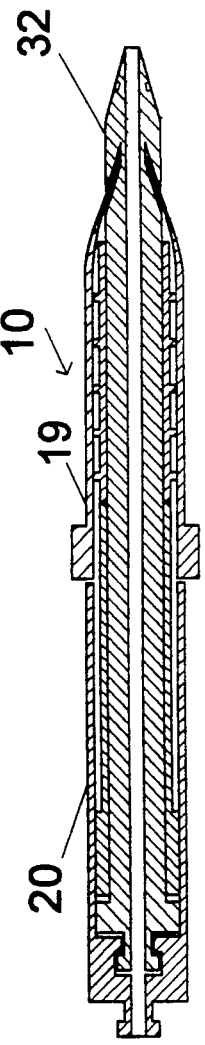
FIGURE 5
FIGURE 6
FIGURE 7
FIGURE 8

INSERTION TOOL FOR AN INTRALUMINAL GRAFT PROCEDURE

BACKGROUND OF THE INVENTION

FIELD OF THE INVENTION

This invention relates to a tool for inserting and deploying a medical graft within a body cavity, such as a blood vessel, and more particularly, to a tool for inserting and deploying such graft in a femoral-popliteal artery during an intraluminal graft procedure.

BACKGROUND INFORMATION

Balloon angioplasty and atherectomy have generally not proven to be viable long term options in the treatment of extensive atherosclerotic lesions in femoral-popliteal arteries. Good results are only obtainable with such methods when the flow limiting lesions are short and discrete. It is thus apparent that patients with extensive occlusive disease in a femoral-popliteal artery are presently best treated by bypass surgery. Conduits for such bypass surgery can be either autogenous, such as saphenous vein, or synthetic, such as tetrafluoroethylene polymer sold under the brand name "Goretex". The choice of the graft type employed depends on the preference of the surgeon and on the integrity of the outflow tract. This technique is an effective long term option, with patency rates in the 80 percent range for selected cases. This procedure is one of the most common graft procedures, with 25,000 to 30,000 cases being treated each year.

In accordance with the standard procedure for providing such a bypass, a surgical cutdown is performed in the groin area and in the leg, thereby providing cutdowns above and below the diseased portion of the blood vessel to be bypassed. A tunnel is made along side the diseased artery between the cutdown areas, and the graft or prosthesis is passed through the tunnel. After the graft or prosthesis is sutured to the femoral end of the artery at the cutdown in the groin area and to the popliteal end of the artery at the lower cutdown, blood flow is restored through the affected leg. This procedure generally takes 2½ to 3 hours, with a recovery time lasting 5 to 6 days. Disadvantages of this procedure include the requisite spinal or general anesthesia, the requirement for two incisions, the length of surgery, with significant morbidity and mortality, and the length of time required for recovery.

DESCRIPTION OF THE PRIOR ART

A number of U.S. patents describe methods for inserting a radially expandable, generally tubular prosthesis, stent or graft in a blood vessel. The prosthesis has a contracted state, in which it is carried to a diseased portion of the blood vessel by means of an insertion tool, and a radially expanded state, which it assumes upon being released by the insertion tool. The insertion tool includes means for holding the prosthesis in its contracted state, whereby narrow and obstructed blood vessels can be traversed. After the deployment, the expansion of the prosthesis forms a central hole suitable for blood flow and, with radial compression forces, seats the prosthesis in place within the blood vessel. After the procedure, the prosthesis continues to be held in place by these compression forces For example, U.S. Pat. No. 4,665,918, issued to Garza et al on May 19, 1987, describes an implant tool having an outer sheath covering the prosthesis and holding it in a contracted state during the insertion procedure The outer sheath is slidably mounted over a delivery catheter and within a tubular outer catheter. At the proximal end of the device, a first pair of locking arms, variable in effective length through attachment at a plurality of notches, is used to determine how far the delivery catheter extends from the outer catheter; and a second pair of locking arms is used to hold the sheath in place over the prosthesis. When the obstructed portion of the blood vessel is reached, this second pair of locking arms is removed, and the outer sheath is pulled outward, uncovering the prosthesis, which expands radially, pushing away obstructive material in the blood vessel and providing a clear central hole, through which the distal tip of the insertion tool is withdrawn.

In another such example, U.S. Pat. No. 4,732,152, issued to Wallstén et al on Mar. 22, 1988, describes an insertion tool having an outer tip portion consisting of a hose folded back within itself, leaving a double-walled cavity in which a prosthesis is held in its contracted state. The hose is connected to a pressurized cylinder, which is slid outward on a central shaft, pulling the fold in the hose outward to expose the prosthesis, which then expands in the blood vessel. Alternative embodiments of the insertion tool include an inflatable balloon ahead, behind, or around the double-walled cavity, provided for widening the blood vessel before the prosthesis is released at a desired location.

U.S. Pat. No. 4,875,480, issued to Imbert on Oct. 24, 1989, describes a means for providing the circulation of a liquid flushing medium to remove gasses, such as air, which might be trapped in the cavity with the prosthesis prior to deployment of the prosthesis. Means are also described for flushing gasses from the folded back part of the hose to eliminate the danger of releasing gasses into the bloodstream in the event of a rupture in the hose.

U.S. Pat. No. 4,771,773, issued to Kropf on Sep. 20, 1989, describes an insertion tool for placing a prosthesis in the form of a helical spring within a blood vessel. In a released, or deployed state the prosthesis has a larger diameter. For insertion the prosthesis is wound, by the rotation of one end, tightly on a mandrel forming a part of the insertion tube, having a diameter smaller than the inner diameter of the prosthesis. Each end of the prosthesis is fastened to one of a pair of axially separated fasteners, which are in turn mutually connected by a transmission in the area of the mandrel. The transmission allows relative rotation of the fasteners only in the direction which tightens the helical prosthesis, until a clutch is actuated to allow rotation in the opposite direction. Alternately, one of the fasteners includes a triggering member which releases the associated end of the helical prosthesis. The clutch or triggering member can be actuated from the end of the insertion tool opposite to the mandrel.

U.S. Pat. No. 5,026,377, issued to Burton et al on Jun. 25, 1991, describes an insertion tool for deploying a self-expanding tubular prosthesis, or stent, which is preferably a braided type, within a body canal, such as a blood vessel. The tool includes an elongated tubular outer sleeve, having disposed therein an elongated core which is movable relative to the sleeve. The core has a grip member, at or near its distal end, which is adapted to releasably hold the prosthesis within the outer sleeve. This grip member, which provides a high-friction contact surface between the prosthesis and the core, may be a sleeve or coating of a material which takes a set, such a polyurethane, attached to the core. The prosthesis is carried through the blood vessel, in a contracted state, being held in an annular space between the grip member and the outer sleeve. When the correct position is found, deployment of the prosthesis is begun by pulling the outer sleeve backward, allowing the distal end of the prosthesis to expand against the walls of the blood vessel. If the position of the prosthesis, which is then checked by fluoroscopy is correct, the outward motion of the outer sleeve is continued to release the entire prosthesis; otherwise the outer sleeve is moved back inward to retract the part of the prosthesis which has been extended, and the prosthesis is repositioned as desired. During these motions, the prosthesis is held in position relative to the core by contact with the grip member.

While the prior art devices described above rely on the release of mechanical energy stored in the prosthesis to provide compressive forces necessary to hold the prosthesis in place, the intraluminal grafting system described in U.S. Pat. No. 4,787,899, issued to Lazarus on Nov. 29, 1988, employs a pressurized expandable membrane, operating inside a generally cylindrical prosthesis within a blood vessel, to force the points of staples fastened to the outside of the prosthesis outward into the walls of the blood vessel. This device is described for use in the repair of a damaged vessel, such as an aneurysm or a torn vessel. The insertion tool includes a flexible rod and a tube arranged to be slid along the axis of the rod. The distal end of the rod mounts a cup, having an open end facing away from the distal tip, in which a collapsed prosthesis is carried, extending around the distal end of the tube. The prosthesis is preferably made of nylon, dacron, or Teflon, having a number of circumferential bifolds along its length. The expandable membrane forms a part of the distal portion of the tube. To deploy the prosthesis, the expandable membrane is inflated, and the tube is pulled outward, dragging the prosthesis out of the cup and forcing it against the walls of the blood vessel The expansion of the prosthesis forms a large enough internal hole to allow the subsequent withdrawal of the cup.

The prior art intraluminal grafting systems described above each require a special type of graft material formable into a compressed state, and releasable into an expanded state. Thus, these systems share the disadvantage of not being adaptable for the deployment of the types of material commonly used in graft procedures, such as the ribbed Goretex tetrafluoroethylene polymer typically used in femoral-popliteal artery bypass operations.

Furthermore, except for the system described in U.S. Pat. No. 4,787,899 to Lazarus, the prior art systems require that the mechanical strain energy stored within the graft material in its contracted state must exert enough pressure on the walls of the blood vessel to hold the prosthesis in place. U.S. Pat. No. 4,787,899 to Lazarus, on the other hand, depends on staples to perform this function. Thus, none of these systems is configured to be used with the common, effective, reliable and approved method of suturing graft material into the healthy portion of a blood vessel. Further, none of the prior art systems can readily utilize commercially available grafts, which have previously been tested and approved by appropriate authorities.

SUMMARY OF THE INVENTION

In accordance with one aspect of the invention, there is provided apparatus for the intraluminal insertion and deployment of a medical graft within a blood vessel. The apparatus includes a shaft having a tapered tip at a distal end and a body extending from the tapered tip to a proximal shaft end. The medical graft is slideably mounted on the body remote from a distal portion of the shaft. The apparatus further includes a sheath having a proximal portion slideably mounted over the medical graft, the sheath having a distal end removably engaging the distal portion of the shaft to form a taper towards the tapered tip of the shaft. The sheath is fixedly maintained over the medical graft and engages the distal portion of the shaft during insertion and the shaft and sheath are removable for deployment of the medical graft.

BRIEF DESCRIPTION OF THE DRAWINGS

Preferred versions of the subject invention are hereafter described with specific reference being made to the following Figures, in which:

FIG. 4 is an axial cross-sectional view of a guide funnel provided as an accessory for the assembly of the tool of FIG. 1;

FIGS. 5 through 8 show the manner of assembling the various components of the tool of FIG. 1;

DETAILED DESCRIPTION

An insertion tool 10 used for performing an intraluminal bypass-type medical procedure in a blood vessel, such as the femoral-popliteal artery, with a conventional and commercially available ringed synthetic graft material, is shown in FIGS. 1 through 8.

Figure 1:
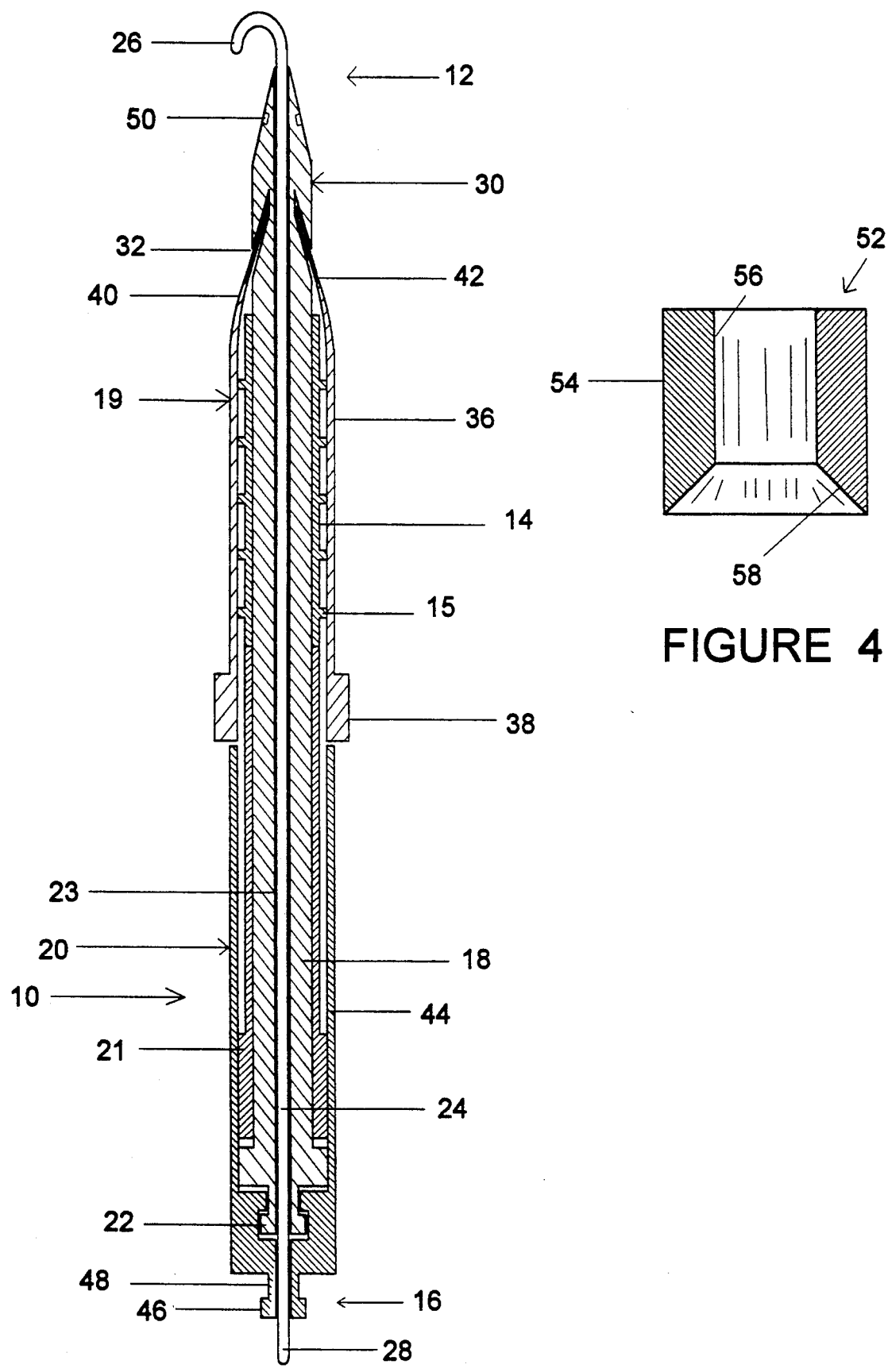
FIG. 1 is an axial cross-sectional view of an intraluminal insertion tool built in accordance with this invention, shown operating on a guide wire.

Referring first to FIG. 1, insertion tool 10 includes a distal end 12, which extends into the human body during the insertion of a synthetic blood vessel graft 14, and a proximal end 16, which remains outside of the human body, and which is used to manipulate the insertion system so that synthetic graft 14 is delivered to the desired location. Graft 14 is preferably made of a synthetic material, such as a tetrafluoroethylene polymer, and is sold under the brand name "Goretex" by W. L. Gore, of Arizona. Graft 14 includes a number of spaced integral rings 15 around its outer surface, for providing stiffness and to prevent collapse in use, while allowing the flexibility required to traverse the vascular system and to bend with subsequent motion of the patient.

Tool 10 is designed to carry graft 14 into the body on an insertion shaft 18, while graft 14 is covered by a shield, or sheath 19, as tool 10 is advanced within the body. When the proper location for graft 14 is attained, a safety lock tube 20, which holds sheath 19 in place during insertion, is disengaged and removed from insertion shaft 18, and sheath 19 is slid outward from the body, off the proximal end of shaft 18, outwardly exposing graft 14. Insertion shaft 18 is then pulled outward from the body, while a deployment slider 21 is held in place, so that graft 14 is deployed, being left in place within the body.

Insertion shaft 18 extends the length of tool 10, having a male fitting 22 of a type which can be rotationally locked or unlocked from a mating female fitting, such as a luer fitting, at a proximal end, permitting the attachment of standard medical accessories, such as syringes or hemostasis valves. Shaft 18 also includes an axial hole 23 extending its entire length to allow the infusion or aspiration of a fluid and/or to allow the passage therethrough of a guide wire 24, which may be of a conventional type having a "J"-shaped hook at a distal end 26 and a straight proximal end 28. Insertion shaft 18 is fabricated from a somewhat flexible material, such as polycarbonate and may have a diameter of approximately six millimeters, or less, thereby permitting a slight flexure during insertion into an removal from the body. The distal end of insertion shaft 18 has a tapered tip 30, which dilates the treatment area of the body as shaft 18 is advanced into the human body. A circumferential slot 32 extends inward around insertion shaft 18 at an angle pointing toward tapered tip 30. Slot 32 may be axially displaced along the cylindrical portion of shaft 18 by between 2.5 to 12.7 millimeters from the adjacent end of tapered tip 30 and the depth of slot 32 may be from 1.3 to 2.5 millimeters.

The length of insertion shaft 18 depends on the procedure to be accomplished, and particularly on the length of the synthetic graft 14 to be inserted. For intraluminal femoral-popliteal artery procedures, a graft 14 may typically be 300 to 350 mm in length. Insertion shaft 18 must be somewhat longer than twice the length of graft 14 to accommodate the remaining components of tool 10 and to allow tool 10 to be manipulated as intended. The diameter of shaft 18 is selected approximate the inner diameter of graft 14 so that graft 14 closely fits over shaft 18.

Figure 2:
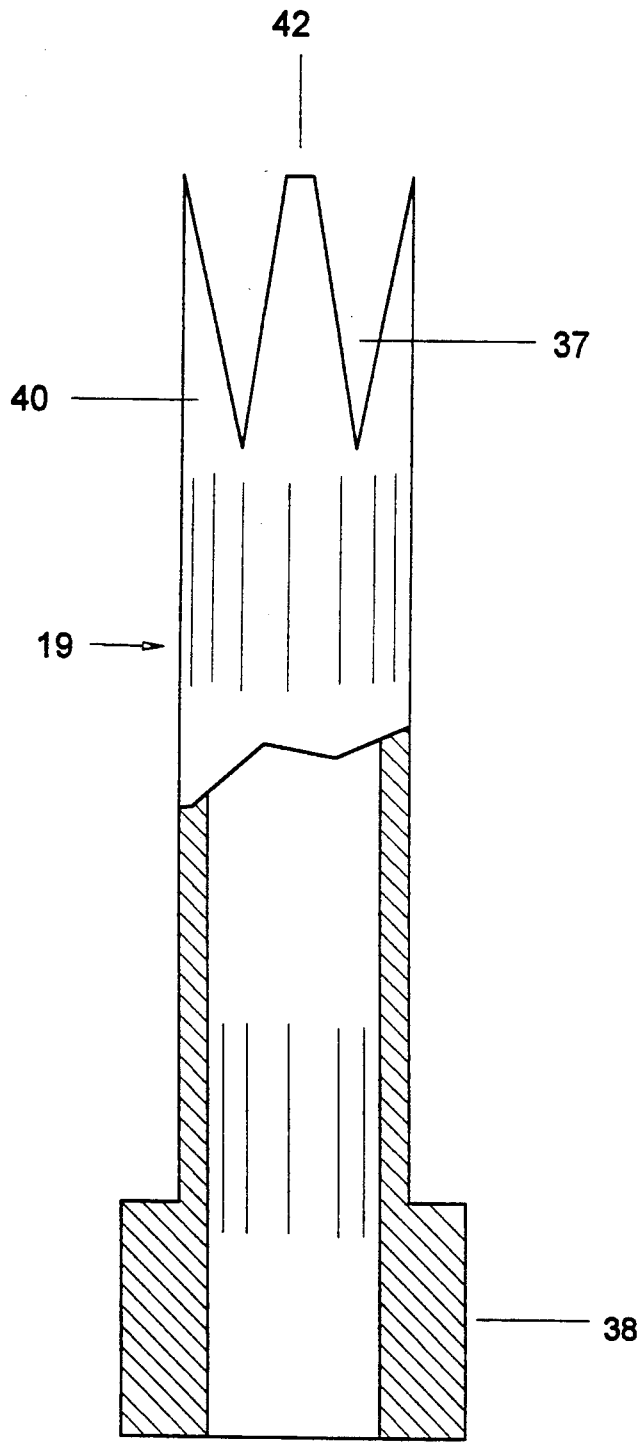
FIG. 2 is a partly sectional side elevation of the sheath used as a part of the tool of FIG. 1.
Figure 3:
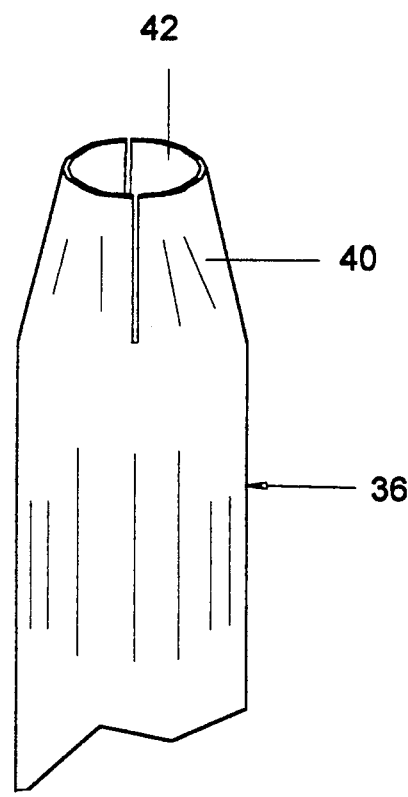
FIG. 3 is an isometric view of the distal tip portion of the sheath of FIG. 2.

FIGS. 2 and 3 show sheath 19 in more detail. Sheath 19 forms the outer portion of insertion tool 10 during the insertion procedure. As seen in FIG. 2, sheath 19 has a thin tubular portion 36 and a relatively rigid collar 38, which, as discussed hereafter, provides a grip for the physician at the proximal end of sheath 19. Four or more Vee shaped cuts 37 are made at the distal end of sheath 38, thereby forming tabs 42 which may thereafter be pressed together to form a tapered end 40, as best seen in FIG. 3, when tabs 42 are inserted in slot 32.

When sheath 19 is assembled on insertion shaft 18 in the manner shown in FIG. 1, tabs 42 fit within slot 32 of shaft 18. A guide funnel 52, seen in FIG. 4, is provided as an accessory to assist in the assembly of tabs 42 into slot 32. Guide funnel 52 has a cylindrical outer surface 54, an axial hole 56, and an internal truncoconical surface 58. After sheath 19 is moved completely past slot 32, guide funnel 52 is placed over tapered tip 30 of shaft 18, to be held in place while sheath 19 is moved toward the distal end of tool 10. This motion causes the inward deflection of tabs 42 upon contacting truncoconical surface 58, so that tabs 42 are simultaneously fed into slot 32. After sheath 19 is slid fully forward, guide funnel 52 is removed from tool 10.

Since sheath 19 covers graft 14 during its advancement into the body on insertion shaft 18, prior to final deployment, sheath 19 must be constructed of a material, such as a tetrafluoroethylene polymer, which slides easily through the body. Alternately, other materials with low friction surfaces or slippery coatings, such as hydrogel, may be used. When flexible tabs 42 are held within slot 32, the distal end of sheath 19 is maintained in a tapered configuration, which permits further dilation of the treatment area of the body through which the insertion tool 10 is advanced. The internal diameter of sheath 19 must be large enough to allow sheath 19 slide over graft 14 during the assembly of tool 10 and during the deployment of graft 14 within the body. To facilitate the advancement of tool 10 through the body, it is desirable that the distance from the inner to outer surfaces of tubular portion 36 be as thin as possible, consistent with requirements for strength and stiffness which may be placed on sheath 19 during the usage of tool 10.

Referring now to FIGS. 5 through 8, the manner of assembling tool 10 and graft 14 is shown. First, as seen in FIG. 5, deployment slider 21 is inserted on shaft 18 and then graft 14 is inserted on shaft 18 in front of slider 21. The resulting subassembly after slider 21 and graft 14 are assembled is seen as the left portion of FIG. 6. As seen, the length of slider 21 and graft 14 substantially equals the length of shaft from fitting 22 to slot 32. Graft 14 is selected to be the appropriate length for the medical procedure to be performed and preferably, the length of deployment slider 21 takes up the remaining available length of shaft 18. Next, as seen in FIG. 6, sheath 19 is inserted over graft 14 and the tabs 42 are inserted into slot 32 using guide funnel 52. At this point, the partially assembled tool 10 appears as in the right portion of FIG. 7. Lastly, as seen in FIG. 7, safety lock tube 20 is slid over deployment slider 21 and against the back end of sheath 19. Then, safety lock tube is rotated 90 degrees and becomes locked with fitting 22 at the proximal end of shaft 18. In this position, safety lock tube maintains tabs 42 of sheath 19 fixedly engaged in slot 32. Now, tool 10 is completely assembled as seen in FIG. 8, and ready for use.

As assembled in FIG. 8, tool 10 is ready for insertion into a body for the purpose of placing graft 14 in the body. For example, graft 14 may be used as a bypass for a blocked artery, such as the femoral-popliteal artery in a patient's leg. The procedure for inserting tool 10 includes first identifying the area to be bypassed. If the bypass area is a blockage in an artery, an inccision is made to expose the lumen of the artery on the proximal side of the blockage. Next, the distal or "J" end 26 of a conventional guide wire 24, as seen in FIG. 1, is inserted within the exposed artery to a point on the distal side of the blockage, with the proximal end 28 of the guide wire 24 remaining outside of the body. Next, tool 10 is guided into the exposed artery by axial hole 23 being inserted over the proximal end 28 of guide wire 24. Tool 10 is then inserted into the interior of the artery through the incision in the artery until the distal end of graft 14 is beyond the blockage. During insertion, tool 10 is guided through the artery by guide wire 24 in a well known manner. In assembling tool 10, the length of graft 14 is selected to be appropriate for the blockage area to be relieved and the length of slider 21 is preferably selected to take up the remaining length of shaft 18. Sheath 19 is further selected to somewhat longer than graft 14, so that when tool 10 is fully inserted, collar 38 of sheath 19 remains outside of the patient's body.

The process of deploying graft 14 into a body begins with safety lock tube 20 being rotated to the unlocked position and then being slidably removed. Then, collar 38 is grasped and sheath 19 is slid outward over deployment slider 21. During this step, tabs 42 are removed from slot 32 and expand to slide over deployment slider 21 as well. After sheath 19 is removed, graft 14 is exposed within the artery, which collapses against the outer surface thereof. The presence of rings 15 particularly maintains graft 14 firmly in place so that it is not easily moved as guide wire 24, slider 21 and lastly shaft 18 are removed. However, to assure that graft 14 remains in position, removal may proceed by the physician holding slider 21 against graft 14 while first removing shaft 18. After shaft 18 is removed, rings 15 provide the strength required to prevent graft 14 from collapsing. After tool 10 is completely removed from the body, the proximal end of graft 14 is preferably attached, by suturing, to a healthy portion of the artery, above the diseased section, and blood flow is restored.

One particular advantage obtained from using tool 10 is that a wide variety of commercially available and thoroughly tested and approved forms of graft material may be used, instead of requiring the use of special forms of graft material having a radially contracted state during insertion and a radially expanded state after deployment, as taught in the prior art. Examples of tools and systems requiring such radially expandable or self-expanding grafts are found in U.S. Pat. No. 4,665,918 to Garza, U.S. Pat. No. 4,732,152 to Wallstén et al, U.S. Pat. No. 4,771,773 to Kropf, U.S. Pat. No. 4,787,899 to Lazarus, U.S. Pat. No. 4,875,480 to Imbert, and U.S. Pat. No. 5,026,377 to Burton et al.

It should be noted that safety lock tube 20 includes a luer type fitting 46 for the attachment to standard medical devices and an axial hole 48 extending through its proximal end and aligned with axial hole 23 when attached. This structure permits the infusion or aspiration of fluid by means of axial hole 23 in insertion shaft 18. During the advancement of tool 10 through a blood vessel, a contrast medium can be infused through axial holes 48 and 23 to allow visualization of tool 10 relative to body structures under fluoroscopy. Placement of the guide wire 24 through axial holes 48 and 23 into the body assists in navigation of tool 10 through the body, thereby increasing the safety of procedures using tool 10 by following well established practices of guide wire navigation. The diameters of axial holes 48 and 23 are large enough to permit the simultaneous extension of a guide wire and fluid motion therethrough.

In one version of insertion tool 10, tapered tip 30 of insertion shaft 18 may include a metal band 50 which becomes visible under fluoroscopy to provide information to the physician regarding the location of tool 10 inside the body. Alternately, tip 30 can be made using a radio-opaque material of many different types.

As noted above, to prepare for the performance of an intraluminal graft procedure a proper length of graft material 14 must be loaded into the tool 10 and the other components have lengths based upon the length of graft and/or the length of shaft 18. It is anticipated that appropriate lengths of graft 14 and deployment slider 21 will be provided in separate, sterile packages, and that a surgeon will typically have several lengths of insertion tools 10 to be used with several corresponding lengths of graft material. Alternately, fully assembled insertion tools 10 may be supplied in sterile packaging with differing lengths of graft 14 pre-loaded therein, ready for the insertion procedure.

As indicated above, one anticipated application of insertion tool 10 is in the treatment of severe occlusive disease in the peripheral arterial system, particularly in the installation of an intraluminal graft in a femoral-popliteal artery. In this procedure, a single incision is made to expose the affected artery and the diseased artery is traversed, employing either a guide wire or an arthrectomy device. In some patients, an angioplasty balloon may first be used to dilate the artery to a diameter of six to seven millimeters. While balloon angioplasty is not generally successful when applied to a lone segment of occluded femoral-popliteal artery as a treatment, it is often a useful initial procedure to open the artery for the subsequent insertion of graft material.

It is anticipated that the medical procedure described herein can be performed under a local anesthetic in one to two hours with a hospitalization of only a few of days. Thus, significant advantages are gained over the conventional procedure, which requires cutdowns to the artery in both the femoral and popliteal locations, the formation of a tunnel space, adjacent to the diseased artery for the deployment of a bypass graft, and suturing of the graft to the artery at both ends. Such conventional procedures, of course, must be done under a general anesthetic and require significantly longer surgical and recovery times.

Figure 9:
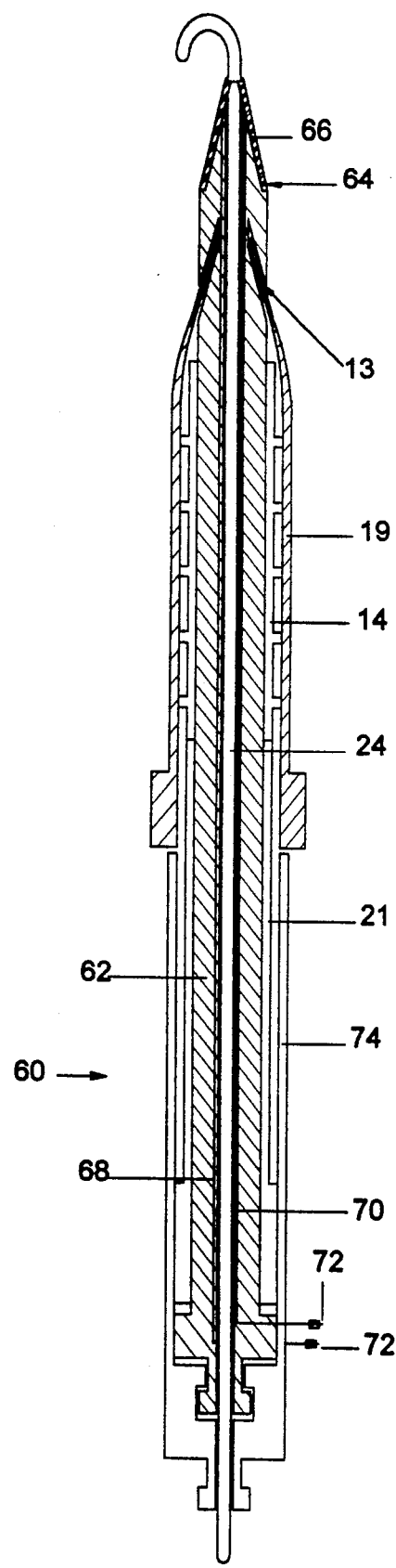
FIG. 9 is an axial cross-section view of an alternative version of the intraluminal insertion tool, including a heated tapered distal section.

Referring now to FIG. 9, an insertion tool 60 is shown having an insertion shaft 62 extended and otherwise modified to provide a tapered tip 64 with a circumferential heating element 66, which may be used to soften the treatment site and to assist in the dilation effect needed to advance tool 60 through the body. The temperature range used at this heating element may be from 40 degrees C to 200 degrees C. Heating element 66 may include an inner layer of electrically resistant material, thereby permitting heating by direct current, covered by metal or of some other material capable of sustaining and transmitting the required heat. In tool 60, insertion shaft 62 is formed of a thermoplastic material molded around electrical wires 70 or around wire lumens extending from electrical connectors 72 to heating element 66. A narrow slot 74, extending longitudinally along the tubular portion of safety lock tube 76, allows the assembly and operation of tube 76 as previously described relative to safety lock tube 20 of insertion tool 10, with wires 70 extending outward to connectors 72 through slot 74. Alternately, heating element 66 may be activated by radio frequency energy as can be appreciated by those skilled in the art.

Electrical connectors 72 provide an interface at which wires 70 are connected to a controllable source of electrical current. A number of well known methods for providing and controlling electrical current can be used to control the temperature of heating element 66. For example, a thermistor (not shown) can be located adjacent to heating element 66 to provide an indication of the temperature, with feedback from the thermistor being used to regulate the electrical current provided to element 66.

Figure 10:
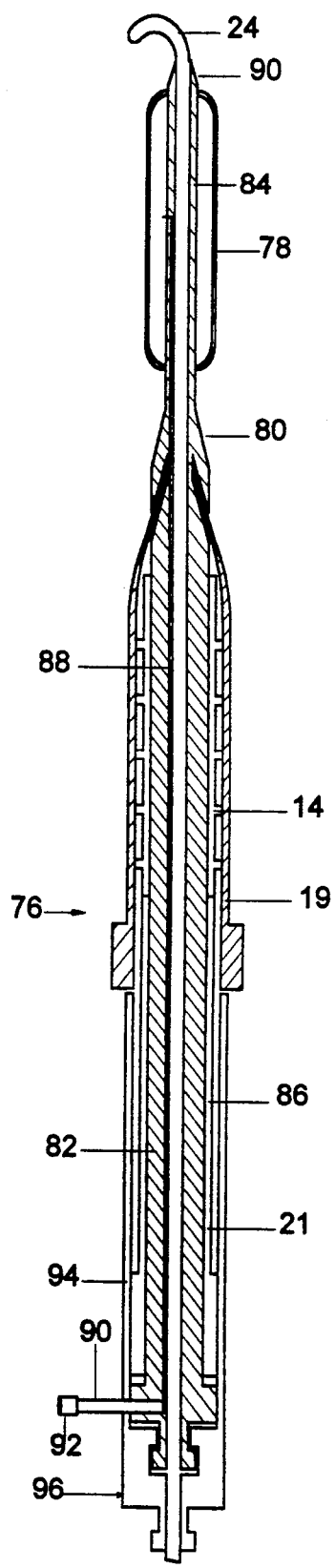
FIG. 10 is an axial cross-sectional view of a second alternative version of the intraluminal insertion tool, including an integral angioplasty balloon.

Referring now to FIG. 10, a cross-sectional view of a second alternative insertion tool 76 is shown. Tool 76 has been modified relative to tool 10 to support an inflatable membrane forming an angioplasty balloon 78 extending from tapered tip 80 of insertion shaft 82. An extended distal cylindrical shaft section 84, having a diameter less than that of main shaft section 86, and a length of 10 to 300 millimeters, is provided for the attachment of balloon 78. A small hole 88, extending along the length of shaft 82, is used to provide a fluid, such as saline solution, water, or contrast media, to inflate balloon 78 at a pressure from one to twenty atmospheres. If insertion shaft 82 is made using a thermoplastic molding process, hole 88 may be provided by including a small diameter multi-lumen extension in the mold as a insert.

Balloon 78 may have an outer diameter of four to thirty millimeters and a length of ten to 200 millimeters and it may be fabricated from irradiated polyethylene, polyvinyl chloride, or other suitable balloon materials well known to those skilled in the angioplasty art. A distal tip 90 of distal shaft section 86 is also tapered, having a profile similar to that of conventional angioplasty catheters. Hole 88 is connected to a tube 90 extending outward to a small luer type fitting 92, which provides a capability for connection to standard medical accessories (not shown). A slot 94 extends along the tubular portion of safety lock tube 96, providing for the installation and removal of tube 96 around outward extending tube 90.

In its anticipated usage, tool 76 provides an additional advantage in simplifying operative procedure by combining the angioplasty procedure required to open the clogged artery, so that the tool can be advanced therethrough, with the advancement of the tool. When compared to the prior art embodiments including angioplasty balloons described in U.S. Pat. No. 4,732,152 to Wallstén et al and U.S. Pat. No. 4,875,380 to Imbert, insertion tool 76 has the advantage of not requiring the use of a radially self-expanding graft. In insertion tool 76, full advantage is taken of the expandable property of angioplasty balloon 78. In its inflated condition, this balloon 76 is capable of opening a blood vessel to a diameter through which tool 76 can pass with the application of a reasonable level of axial force. In its deflated condition, balloon 76 is small enough to pass through the central hole in graft 14. Thus, standard graft materials, not having a self-expanding characteristic, can be used for graft 14, and the complexity included in the Wallstén et al design, required to deploy a self-expanding graft pushing outward on its covering, is not required.

While the invention has been described in its preferred forms or embodiments with some degree of particularity, it is understood that this description has been given only by way of example and that numerous changes in the details of construction, fabrication and use, including the combination and arrangement of parts, may be made without departing from the spirit and scope of the invention.

What is claimed is:

1. Apparatus for the intraluminal insertion and deployment of a medical graft within a blood vessel comprising:
   a shaft having a tapered tip at a distal end and a body extending from said tapered tip to a proximal shaft end, said medical graft being slideably mounted on said body remote from a distal portion of said shaft; and
   a sheath having a proximal portion slideably mounted over said medical graft, said sheath having a distal end removably engaging said distal portion of said shaft to form a taper towards said tapered tip of said shaft;
   said sheath being fixedly maintained over said medical graft and engaging said distal portion of said shaft during insertion and said shaft and sheath being removable for deployment of said medical graft.

2. The apparatus of claim 1:
   wherein said distal portion of shaft includes a circumferential slot near said tapered tip; and
   wherein said distal end of said sheath is divided into a plurality of tabs extending into said circumferential slot.

3. A kit comprising the apparatus of claim 2 and an assembly tool having a cavity for placement over said tapered tip to direct said tabs into said circumferential slot.

4. The apparatus of claim 1, further including a safety means removably attached to a proximal portion of said shaft for preventing motion of said sheath toward said proximal shaft end.

5. The apparatus of claim 4:
   wherein said apparatus further includes a deployment slider positioned between said medical graft and said proximal portion of said shaft for maintaining the position of said medical graft on said shaft during removal of said sheath;
   wherein said proximal shaft portion includes a first side of a locking mechanism; and
   wherein said safety means includes a tubular structure covering said deployment slider, extending between said proximal shaft portion and a proximal end of said sheath, said safety means further including a proximal end with a second side of said locking mechanism, said second side mating with and releasably engaging said first side of said locking mechanism.

6. The apparatus of claim 1:
   wherein said shaft includes a first locking fitting extending from said proximal shaft end; and
   wherein said shaft includes an axial aperture extending therethrough from said locking fitting to said tapered tip.

7. The apparatus of claim 6, further including a safety tube removably engaging said first locking fitting and extending towards said sheath for preventing motion of said sheath toward said proximal shaft end, said safety tube further including a second locking fitting extending from a proximal end thereof.

8. The apparatus of claim 1, further including an electrical heating element at said tapered tip and means for providing electrical current to said heating element.

9. The apparatus of claim 8, further including a temperature sensing device at said tapered tip, providing an output signal indicating a temperature measured at said tapered tip and means for controlling electrical current provided to said heating element in response to said output signal.

10. The apparatus of claim 1, wherein said medical graft is a hollow cylinder with a plurality of integral, axially spaced rings extending from an outer surface thereof.

11. Apparatus for the intraluminal insertion and deployment of a medical graft within a blood vessel comprising:
    a shaft with a tapered distal tip, a first, second and third integral and adjacent aligned cylindrical portions extending proximally from said tapered distal tip to a proximal shaft end, said medical graft being slidably positioned on said shaft around said second cylindrical portion;
    a deployment slider slideably positioned on said shaft around said third cylindrical portion;

a sheath having a proximal portion slideably mounted on said deployment slider and on said medical graft, and a distal portion having a releasable tapered end removably engaging said first cylindrical portion, wherein movement of said sheath proximally towards said proximal shaft end disengages and releases said sheath tapered end and uncovers said medical graft; and removable means for locking said sheath in engagement with said first cylindrical portion.

12. The apparatus of claim 11:
wherein said first cylindrical portion of shaft includes a circumferential slot; and
wherein said distal portion of said sheath is divided into a plurality of tabs extending into said circumferential slot.

13. The apparatus of claim 12, wherein said medical graft comprises a hollow cylinder with a plurality of integral, axially spaced rings extending from an outer surface thereof.

14. Apparatus for providing a clear passageway within a blood vessel through angioplasty, and for the intraluminal insertion and deployment of a medical graft within said blood vessel, said apparatus comprising:
a shaft with a tapered distal tip, a first cylindrical portion extending proximally from said tapered distal tip, a tapered intermediate section extending proximally from said first cylindrical portion, and a second cylindrical portion extending proximally from said intermediate tapered section to a proximal shaft end; and surrounding said first cylindrical portion;
fluid supply means including a fluid port at a proximal end of said shaft and a conduit through said shaft between said fluid port and said first cylindrical portion;
a deployment slider slideably mounted on a proximal portion of said second cylindrical portion;
a medical graft slideably mounted on a distal end of said second cylindrical portion, adjacent said deployment slider, said medical graft having an axial hole large enough to slide over said inflatable membrane with said inflatable membrane in a deflated state; and a sheath having a proximal portion slideably mounted on said deployment slider and on said medical graft, and a tapered distal section removably engaging a distal portion of said second, cylindrical surface, wherein movement of said sheath proximally over said proximal shaft end uncovers said medical graft.

15. The apparatus of claim 14:
wherein an outer surface of said second cylindrical portion includes a circumferential slot near said intermediate tapered section; and
wherein said tapered distal section of said sheath is divided into a plurality of tabs extending into said circumferential slot.

16. The apparatus of claim 14:
wherein said medical graft comprises a hollow cylinder with a plurality of integral, axially spaced rings extending from an outer surface thereof.

17. The apparatus of claim 14, further including safety means removably attached to a proximal portion of said second cylindrical portion for preventing motion of said sheath toward a proximal end of said apparatus until said safety means is removed.

18. The apparatus of claim 17:
wherein said proximal shaft end includes a first side of a locking mechanism; and
wherein said safety means includes a tubular structure covering said deployment slider, extending between said proximal shaft end and a proximal end of said sheath, said safety means further including a proximal end with a second side of said locking mechanism, said second side mating with and releasably engaging said first side of said locking mechanism.

19. The apparatus of claim 14, wherein said shaft includes a first locking fitting extending from said proximal shaft end and an axial aperture extending therethrough from said locking fitting to said tapered distal tip.

20. The apparatus of claim 19, further including a safety tube removably engaging said first locking fitting, wherein said safety tube includes a tubular portion extending over said deployment slider to a proximal end of said sheath, a second locking fitting extending from a proximal end thereof, and an aperture extending through said second locking fitting.

* * * * *